(12) United States Patent
Kaiser et al.

(10) Patent No.: US 11,083,888 B2
(45) Date of Patent: Aug. 10, 2021

(54) ELECTRODE LEAD WITH VARIABLE, INCREMENTALLY ADJUSTABLE FIXING LENGTH

(71) Applicant: BIOTRONIK SE & Co. KG, Berlin (DE)

(72) Inventors: Dajana Kaiser, Berlin (DE); Detmar Jadwizak, Erkner (DE); Carsten Fruendt, Berlin (DE); Gordon Hillebrand, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 77 days.

(21) Appl. No.: 16/424,592

(22) Filed: May 29, 2019

(65) Prior Publication Data
US 2019/0374769 A1 Dec. 12, 2019

(30) Foreign Application Priority Data
Jun. 7, 2018 (DE) ...................... 10 2018 113 593.9

(51) Int. Cl.
*A61N 1/04* (2006.01)
*A61N 1/05* (2006.01)
*A61N 1/362* (2006.01)

(52) U.S. Cl.
CPC ........... *A61N 1/057* (2013.01); *A61N 1/0563* (2013.01); *A61N 2001/0585* (2013.01)

(58) Field of Classification Search
CPC ............ A61N 2001/0585; A61N 1/057; A61N 1/0563; A61N 1/362; A61N 1/0488; A61B 5/283; A61B 5/288; A61B 5/29

USPC .......................................................... 607/125
See application file for complete search history.

(56) References Cited

U.S. PATENT DOCUMENTS

| 5,170,802 A | 12/1992 | Mehra |
| 5,246,014 A * | 9/1993 | Williams ................. A61N 1/05 607/122 |
| 5,387,233 A | 2/1995 | Alferness et al. |
| 5,411,546 A | 5/1995 | Bowald et al. |
| 5,476,498 A | 12/1995 | Ayers |
| 6,161,029 A * | 12/2000 | Spreigl ................. A61B 5/042 600/375 |

(Continued)

FOREIGN PATENT DOCUMENTS

| DE | 10153842 A1 | 5/2003 |
| EP | 0546414 B1 | 4/1997 |

(Continued)

OTHER PUBLICATIONS

German Search Report for German Case No. DE 10 2018 113 593.9, dated Aug. 22, 2018 (8 pages).

*Primary Examiner* — Carl H Layno
*Assistant Examiner* — Anh-Khoa N Dinh
(74) *Attorney, Agent, or Firm* — Buchanan Ingersoll & Rooney PC (57) ABSTRACT

An electrode lead for the coronary sinus, having a lead body, which has a distal portion for insertion into the coronary sinus, and at least one electrode for contacting bodily tissue, wherein the at least one electrode is arranged on the distal portion of the lead body. The electrode lead, in order to fix the electrode lead in a blood vessel, has a fixing device, which is connected to a distal end of the lead body, wherein the fixing device is designed to be shortened incrementally or lengthened incrementally.

10 Claims, 7 Drawing Sheets

(56) References Cited

U.S. PATENT DOCUMENTS

| | | |
|---|---|---|
| 2003/0105513 A1* | 6/2003 | Moriuchi ............... A61F 2/915 623/1.15 |
| 2004/0059404 A1 | 3/2004 | Bjorklund et al. |
| 2006/0036307 A1 | 2/2006 | Zarembo et al. |
| 2007/0239247 A1 | 10/2007 | Camps et al. |
| 2008/0132984 A1* | 6/2008 | Schell ................... A61N 1/056 607/121 |
| 2010/0256719 A1 | 10/2010 | Bjorklund et al. |
| 2011/0106099 A1 | 5/2011 | Duffy et al. |
| 2013/0116767 A1* | 5/2013 | Manova ............... A61N 1/0587 607/130 |
| 2015/0112415 A1 | 4/2015 | Weitzig et al. |
| 2015/0306380 A1 | 10/2015 | Sommer et al. |

FOREIGN PATENT DOCUMENTS

| | | |
|---|---|---|
| WO | 9407564 A2 | 4/1994 |
| WO | 9842403 A1 | 10/1998 |

\* cited by examiner

ELECTRODE LEAD WITH VARIABLE, INCREMENTALLY ADJUSTABLE FIXING LENGTH

TECHNICAL FIELD

The present invention relates to an electrode lead that is connectable to a pulse generator and that has electrodes for contacting bodily tissue for cardiac resynchronization therapy ("CRT").

BACKGROUND

Within the scope of the present invention the term "electrode lead" is understood to mean a lead comprising at least one electrical conductor or a plurality of electrical conductors, together with the encasing insulation material, which electrically insulates the electrical conductor(s) outwardly, and as applicable with respect to one another, and also all further functional elements that are fixedly connected to the lead.

The electrode lead generally comprises, at its distal portion, at least one electrode pole (referred to hereinafter as an electrode), which for example can be formed as a ring electrode and by means of which the electrical energy is introduced from the conductor(s) into the tissue to be treated. The at least one electrode can be formed as a pick-up electrode, stimulation electrode or measurement electrode.

The electrode lead generally also has, for example at its proximal end, a connection device (for example a plug), a means of which the electrode lead can be connected releasably or fixedly to an active medical implant, such as a pulse generator, wherein the connection device of the electrode lead for this purpose is connectable to a corresponding counter piece (for example a socket) of the active medical implant.

The connection device of the electrode lead has one or more connectors (for example one or more contacts), wherein each connector can be connected to an electrical conductor of the electrode lead, wherein this conductor can also consist of a plurality of conductors which are guided in parallel and are insulated with respect to one another. Accordingly, in the counter piece to the connection device of the electrode lead on the implant, there is provided a connector of the counter piece for each connector of the electrode lead.

A particularly simple fixing technique for avoiding dislocations of electrode leads of this kind in the coronary sinus region is a wedging of the distal end of the lead body in a vessel. Here, the electrode lead is advanced for example into the vein branches of the coronary sinus until the distal end of the lead body becomes stuck in the tapering vein and assumes a "wedge position". In this position, the vein is closed by the electrode lead.

The possibility to achieve good positioning of the electrical contacts (electrodes) of the electrode lead alongside secure fixing of the electrode lead by means of a wedge position of this kind is heavily dependent on the geometry (for example the profile, the length and the diameter, etc.) of the target vein in the coronary sinus. The end position of the stimulation and/or sensing electrode(s) is therefore usually predefined by the geometry of the target vein and does not necessarily correspond to the best location for the therapy.

Reference is made to the prior art, for example to documents International Publication No. WO 98/42403 or U.S. Pat. No. 5,170,802. These documents disclose a fixing device having what is known as a stem, which is expanded when the electrode lead is situated at the desired position in the vessel. The lead body is securely clamped in the position by the expansion of the stent structure. A disadvantage of this solution is that the fixing is not reversible, which makes it difficult to release and reposition the electrode lead, which is sometimes necessary, following a first fixing, and also to remove the electrode lead.

International Publication No. WO 94/07564 discloses a solution for the problem of repositionability, in which the fixing is realized by an expandable or self-expanding wire cage. A disadvantage of this design is that the wires can cut into the vessel wall and therefore can be very traumatic.

U.S. Pat. No. 5,411,546 lastly presents various solutions for the fixing in a vessel, for example wire spirals that can be reversibly deployed from the catheter sleeve and retracted there-into again. However, due to the small diameter of the wires and the associated small contact area between spiral and vessel wall and the only limited clamping force with which the spiral may be pressed against the vessel wall so that the latter is not damaged, the fixing is not very reliable. The wire designs also disclosed in the document are—as already mentioned above—highly traumatic. Furthermore, what is known as a "sail design", which is not reversible, is also presented in this prior art document.

Reference is also made to United States Publication No. 2006/0036307. This discloses implantable cardiovascular cardiac pacemaker or defibrillator electrode devices, which comprise an elongate, tubular electrode body and a fixing zone in the distal end region of the electrode body. The fixing zone has an outwardly closed peripheral sleeve and is used to releasably fix the electrode device in a body lumen since it is reversibly expandable. The expansion or contraction is controlled by an expansion means arranged in the fixing zone.

In addition to these features, European Patent No. EP 0 546 414 presents an electrode device in which the expansion means is formed by pneumatic or hydraulic pressure application, with the aid of which the wall of the electrode body, which is flexible the fixing zone, is reversibly expandable. However, a permanently tight wall is difficult to produce, and it has therefore been found that the expanded form and therefore the fixing of the referenced solutions decreases over time. Furthermore, the expansion force of the flexible wall is limited.

The present invention is directed at overcoming one or more of the above-mentioned problems.

SUMMARY

On this basis, an object of the present invention is to create an electrode lead that is improved in respect of the above-mentioned problems.

At least this problem is solved by an electrode lead having the features of claim 1. Preferred embodiments of the present invention are detailed in the corresponding dependent claims and will be described hereinafter.

According to claim 1, an electrode lead for the coronary sinus is disclosed, having: a lead body, which has a distal portion for insertion into the coronary sinus, and at least one electrode for contacting bodily tissue, wherein the at least one electrode is arranged on the distal portion of the lead body.

In accordance with the present invention it is provided that the electrode lead, in order to fix the electrode lead in a blood vessel, has a fixing device which is connected to a distal end of the lead body, wherein the fixing device can be shortened incrementally or can be lengthened incrementally.

Within the scope of the present invention, "proximally" means a closer proximity to the pulse generator (along the electrode lead) to which the electrode lead is connectable or connected, whereas "distally" signifies a greater distance along the electrode lead to the pulse generator.

A solution according to the present invention advantageously enables, with a given (optimal) position of the at least one electrode in the coronary sinus, simultaneously a secure fixing of the electrode lead in a target vein of the coronary sinus by the incrementally adjustable length of the fixing device along a longitudinal axis of the electrode lead.

An optimal electrode position and at the same time an optimal fixing position of the electrode lead or of the fixing device in the target vein can hereby be selected.

This also means that, on account of the present invention, the otherwise necessary selection of the fixing variant and of the distances of the electrodes from one another can be spared. Due to the variability of the fixing device, it is possible to dispense, in particular, with the frequent use of multipolar (2-, 3-, . . . , n-pole) electrode leads, which with non-adjustable fixing offer a greater selection in respect of the electrode positions, but are less economical on account of the greater number of electrodes.

The present invention also advantageously offers the possibility to adjust the fixing length of the electrode lead incrementally intraoperatively by few hand movements.

Different curve and fixing geometries can also be produced by the selection and arrangement of the individual segments (see below).

In accordance with a preferred embodiment of the present invention, it is provided that the fixing device has a plurality of interconnected segments in order to incrementally shorten the fixing device, wherein each two adjacent segments can be separated from one another in order to incrementally shorten the fixing device. In accordance with an embodiment of the present invention, the individual segments may each have an identical design. In accordance with an embodiment of the present invention, the individual segments may each vary in their length.

In accordance with an embodiment of the present invention, it is also provided that, for each two adjacent segments, one of the segments has a proximal end portion, which is fixedly connected to a distal end portion of the adjacent segment.

In accordance with an embodiment of the present invention, the individual segments of the fixing device for incrementally shortening the fixing device are designed such that the individual segments can be separated from one another by cutting by means of a cutting tool (for example scalpel or scissors).

In accordance with an embodiment of the present invention, each segment has an x-ray marker at its proximal end portion or at its distal end portion. The position of the x-ray marker in the segment is preferably visible to the eye, and more preferably a different color is selected for each x-ray marker of a segment of the fixing device.

On account of the x-ray markers, in the inserted state the exact position of the fixing device and therefore the electrode(s) in the blood vessel, preferably in a vein branch of the coronary sinus, can be determined by means of x-ray imaging. In the case of blood vessels that taper in the distal direction as seen from the electrode lead, it may be that the electrode(s) cannot be advanced far enough due to the length of the fixing device. In such a case the number of segments to be removed from the fixing device can be determined by counting the x-ray markers. After removal, the fixing device of the electrode lead can be shortened, for example by separating individual segments from the fixing device, for example by means of a cutting tool (for example scalpel or scissors). The x-ray markers visible to the eye make it possible to locate the separation position. If the lead is shortened by means of a cutting tool, the lead is separated preferably proximally of the visible x-ray marker in the event that x-ray markers are arranged at the proximal end portion of the segment, or preferably distally of the visible x-ray marker in the event that x-ray markers are arranged at the distal end portion of the segment. Due the now shortened fixing device, the electrode(s) can be advanced further into the blood vessel when the electrode lead is reinserted.

In accordance with an embodiment of the present invention, it is also provided that the fixing device is conical in the region of the severing position, wherein the narrower end of the cone points in the distal direction and the thicker end of the cone points in the proximal direction in relation to the electrode lead. The conical design in the region of the separation position has the advantage that, once the segments have been separated by a cutting tool, a narrower distal end of the fixing device is provided as compared to the further profile of the outer shape of the fixing device connected to the lead body. This narrower end of the fixing device facilitates the insertion of the distal end of the fixing device of the electrode lead into a catheter and the advancing of the electrode lead in a blood vessel, for example in a vein branch of the coronary sinus.

In accordance with an embodiment of the present invention, it is also provided that, for each two adjacent segments, one of the segments has a proximal end portion, which is connected to a distal end portion of the adjacent segment via a force-fit and/or form-fit connection for separating the two adjacent segments.

In accordance with an embodiment of the present invention, said connection for severing the two adjacent segments is a clamp connection or a latching connection or a bayonet connection. The connection in question is preferably also sealed by means of one or more sealing faces.

In accordance with an embodiment of the present invention, it is furthermore provided that, for each two adjacent segments, one of the segments has a proximal end portion, which is connected to a distal end portion of the adjacent segment, wherein the gap between the two segments at the connection points at the surface of the segment between the two segments has a gap width of at most 0.5 mm, preferably of at most 0.3 mm, and more preferably of at most 0.1 mm.

Due to the preferably small gap width at the connection points between two segments of the fixing device, the electrode lead is prevented from becoming fixed, during the ingrowth process, by tissue which grows into this gap, in such a way that it is no longer possible to remove the lead in the event of a potentially necessary explanation or in such a way that the lead can be removed only with substantial difficulty.

It is furthermore provided in accordance with an embodiment of the present invention that, for each two adjacent segments, one of the segments has a proximal end portion, which is connected to a distal end portion of the adjacent segment via a sealing face.

In accordance with an alternative embodiment of the present invention, it is provided that, for incremental lengthening of the fixing device, at least one segment or a plurality of segments connectable or connected to one another is provided, wherein the at least one segment or the plurality of segments is connectable to a distal end portion of the fixing device via a force-fit and/or form-fit connection. Here as well the individual segments in accordance with an embodiment of the invention can each have an identical design. Furthermore, the length of the individual segments may vary.

In accordance with an embodiment of the present invention, said connection is a clamped connection or a latching connection or a bayonet connection. The connection in question is preferably also sealed by means of one or more sealing faces.

It is furthermore provided in accordance with an embodiment of the present invention that, for each two adjacent segments, one of the segments has a proximal end portion, which is connectable or connected to a distal end portion of the adjacent segment via a force-fit and/or form-fit connection. In accordance with an embodiment said connection can be a clamped connection or a latching connection or a bayonet connection. The connection in question is furthermore preferably sealed by means of one or more sealing faces arranged in the inner lumen.

It is furthermore provided in accordance with an embodiment in respect of the above-described segments, that each segment has a distal end portion which has a sleeve which is designed to form a stop for a mandrel insertable into the electrode lead, so that the fixing device is movable by means of the mandrel and/or can be wedged by means of the mandrel in order to fix the fixing device, i.e. can be advanced into the blood vessel in order to anchor the fixing device there. Said sleeve is preferably made of metal. Typical materials for the sleeve can be, for example, the alloys of nickel-cobalt MP35N or platinum-iridium Pt/Ir 90/10, which are widespread in the field of medical technology.

It is furthermore provided in accordance with an embodiment of the present invention in respect of the above-described segments that the segments each have a lumen, wherein the lumens, in an interconnected state of the segments, form a continuous lumen for receiving a mandrel. This continuous lumen is preferably connected to a lumen of the lead body, so that the mandrel can be inserted via the lumen of the lead body into said continuous lumen of the segment/fixing device.

It is furthermore provided in accordance with an embodiment in respect of the above-described segments, that each segment has a distal end portion which has a seal arranged in the lumen of the segment. The seal is provided in order to seal off the lumen outwardly, so that no blood can infiltrate the lumen. The seal is preferably arranged in the segment that is arranged distally of the stop. The seal is more preferably provided within the sleeve arranged at the distal end portion of the segment.

It is furthermore provided in accordance with an embodiment of the present invention that at least one of the segments of the fixing device, in order to fix the fixing device in the blood vessel, has a predefined form, which can be set straight by inserting a mandrel into the lumen of the at least one segment, wherein the at least one segment assumes the predefined form following the removal of the mandrel from the lumen of the at least one segment.

The predefined form can correspond to one of the following forms: a curved form, a helix, an S curve, a meandering structure, a J curve.

A plurality of segments may also have a predefined form which can be set straight as described above, wherein adjacent segments also together can have or can form one of the aforementioned predefined forms.

If a mandrel is arranged in the continuous lumen of the segments, the predefined forms are set straight to a linear (non-curved) form.

A predefined form which can be assumed by one or more of the segments following removal of the mandrel may furthermore be both two-dimensional and three-dimensional.

It is furthermore provided in accordance with an embodiment of the present invention, that the stop formed by the sleeve narrows the cross-section of the lumen running through the segments, so that a passage which has a narrowed cross-section as compared to the cross-section of the lumen extends through the stop. Besides the diameter or the clear width, the cross-sectional area can also be used as a measure for determining the cross-section. The segments of the fixing device are preferably arranged such that the cross-sectional area of the passage through the stop reduces along the electrode lead from a proximal end to a distal end from stop to stop. The cross-sectional area of the passage preferably has a substantially circular or elliptical design through the stop. Furthermore, the passage through the stop is preferably a central, axial bore through a preferably cylindrical sleeve.

It is furthermore provided in accordance with an embodiment of the present invention, that a mandrel used to advance the electrode lead into the blood vessel and to wedge the electrode lead in the blood vessel has a cross-section at its distal end such that the mandrel is engaged with the stop of the segment arranged at the distal end of the fixing device of the electrode lead when the mandrel is inserted coming from the proximal end into the lumen of the electrode lead, in such a way that the electrode lead can be advanced by the mandrel along its longitudinal axis in the distal direction. In order to adapt the cross-section of the mandrel at its distal end, the mandrel preferably has a thrust element there. The cross-section of the mandrel at the distal end can be adjusted by the thrust element, independently of the cross-section of the shaft of the mandrel. The thrust element of the mandrel is preferably formed as a thickened portion of the shaft at or in the vicinity of the distal end of the mandrel, wherein the thickened portion can be formed more preferably as a sphere or as a cylinder or cone arranged coaxially with the shaft of the mandrel.

The thrust element of the mandrel is preferably designed such that, as considered from the proximal end of the electrode lead, it can be guided through all passages of the stops of the segments arranged before the stop of the segment at the distal end of the fixing device, however it cannot pass through the passage of the stop of the segment arranged at the distal end of the fixing device, such that it can be brought into engagement with the stop of the segment arranged at the distal end of the fixing device. If the segments which in order to lengthen the fixing device are added thereto or in order to shorten the fixing device are separated therefrom have stops with passages of differently sized cross-sectional areas, each segment is then assigned a mandrel having a thrust element which cannot pass through the passage of this segment, but which can pass through the passages of the stops of the segments arranged proximally of this segment. A set of mandrels in which the cross-sectional areas of the thrust elements are matched accordingly to the stops of the fixing device and the segments connected thereto is preferably provided for the electrode lead.

It is furthermore provided in accordance with an alternative embodiment of the present invention, that a mandrel used to advance the electrode lead into the blood vessel and to wedge it in the blood vessel has a thrust element along its shaft, so that the mandrel is engaged with the stop arranged at the proximal end of the fixing device of the electrode lead when the mandrel is inserted coming from the proximal end into the lumen of the electrode lead, in such a way that the electrode lead can be advanced by the mandrel along its longitudinal axis in the distal direction. The mandrel is preferably formed here such that the part of the shaft of the mandrel arranged distally of the thrust element corresponds in respect of its length to the length of the segments connected to the electrode lead. If the electrode lead is shortened by separating a segment from the fixing device, or is lengthened by adding a segment to the fixing device, the part of the shaft of the mandrel arranged distally of the thrust element thus has to be adapted in respect of its length to the modified length of the fixing device. The part of the shaft of the mandrel arranged distally of the thrust element more preferably does not protrude beyond the distal end of the fixing device—even during the insertion of the electrode lead. A set of mandrels in which the lengths of the parts of the shaft of the mandrel arranged distally of the thrust element are matched accordingly to the length of the fixing device and the segments connected thereto is preferably provided for the electrode lead.

It is furthermore provided in accordance with an embodiment of the present invention that the segments have a surface structure (for example a screw structure or alternately arranged protrusions and indentations) for anchoring in the blood vessel.

It is furthermore provided in accordance with an embodiment of the present invention, that the electrode in question is connected to an electrical conductor which is arranged in an interior of the lead body, wherein the corresponding electrical conductor extends helically around the lumen of the lead body, which is designed to receive a mandrel (see also above).

It is furthermore provided in accordance with an embodiment of the present invention that, in the case of two or more electrical conductors, the electrical conductors are arranged co-radially relative to one another. Here, in particular the individual electrical conductors are wound in a manner insulated from one another to form a multiple helix, in which the two electrical conductors form congruent helices of equal diameter and equal pitch, which engage in one another.

It is furthermore provided in accordance with an embodiment of the present invention, that the electrical conductor(s) is/are arranged coaxially with the longitudinal axis of the electrode lead and, in the case of a plurality of electrical conductors, furthermore coaxially with one another, wherein the two conductors are insulated with respect to one another. The coaxial electrical conductor thus formed preferably extends around the lumen of the lead body, which is designed to receive a mandrel.

In accordance with a further embodiment of the present invention, the conductor can also be formed as a cord, wherein the cord can run in its own lumen. A plurality of cords can also be used, in order to provide, in the case of a plurality of electrodes, a separate feed line for each electrode. The plurality of cords are preferably insulated with respect to one another. The insulation can be provided, for example, in that the individual cords are guided in their own lumen.

It is furthermore provided in accordance with an embodiment of the present invention, that the lead body has a proximal end, wherein a connection device for connecting the electrode lead to an implantable pulse generator is arranged at the proximal end, and wherein the electrical conductor in question is connected to an associated contact of the connection device.

A further aspect of the present invention relates to a medical kit with an electrode lead according to the invention and with a plurality of different mandrels for insertion into the electrode lead, wherein in particular each mandrel is provided for use with the electrode lead with precisely one set length of the fixing device.

Additional features, aspects, objects, advantages, and possible applications of the present invention will become apparent from a study of the exemplary embodiments and examples described below, in combination with the Figures, and the appended claims

DESCRIPTION OF THE DRAWINGS

Further features, advantages and embodiments of the present invention will be described hereinafter with reference to the drawings, in which.

DETAILED DESCRIPTION

The realization of the present invention will be described hereinafter on the basis of electrode leads 1 according to the present invention, which are suitable for use in blood vessels of the coronary sinus and which have two electrodes 12, 13 for contacting bodily tissue. Electrode leads 1 of this kind are also referred to as bipolar electrode leads 1. They allow, on the one hand, bipolar stimulation of the target region with the electrodes 12, 13 and, on the other hand, unipolar stimulation at the two positions of the electrodes 12, 13. However, the present invention can also be realized with electrode leads 1 having just one electrode (unipolar electrode lead) with more than two electrodes multipolar electrode lead). A multipolar electrode lead is also understood to mean an electrode lead that has two or more electrode pairs for bipolar stimulation at different positions. Two electrodes can be considered to be an electrode pair if their distance from one another is shorter than the shorter distance between one electrode of the pair to an electrode adjacent to the pair.

Figure 1:
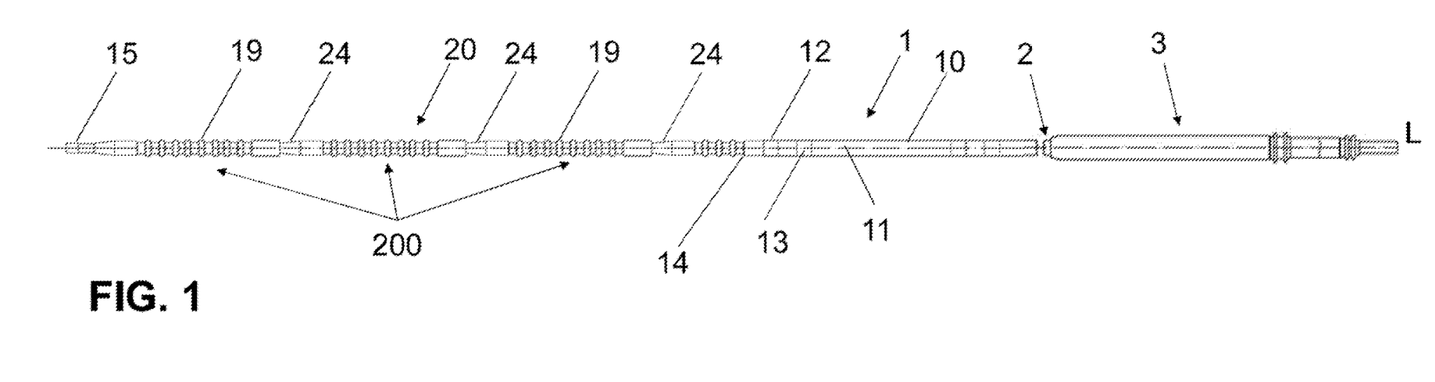
FIG. 1 shows a depiction of an embodiment of an electrode lead with a fixing device that can be shortened incrementally.
Figure 2:
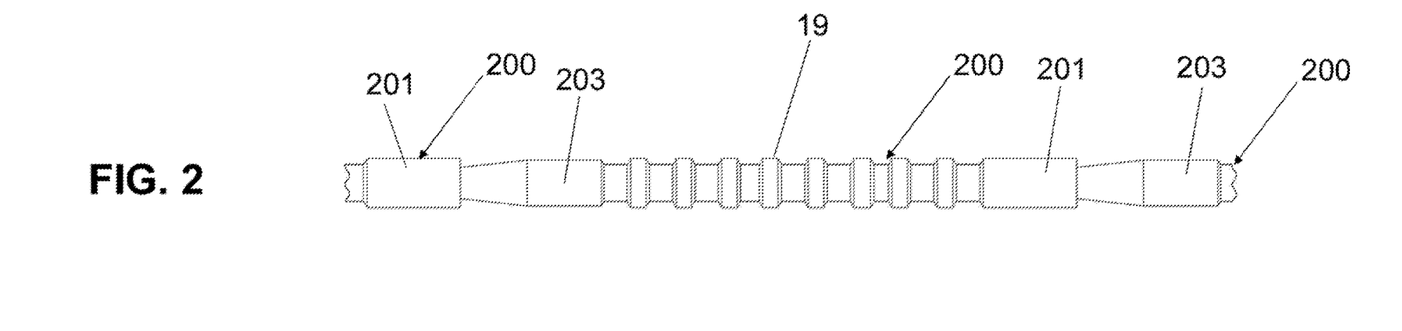
FIG. 2 shows a depiction of a segment of the fixing device according to FIG. 1.
Figure 3A:
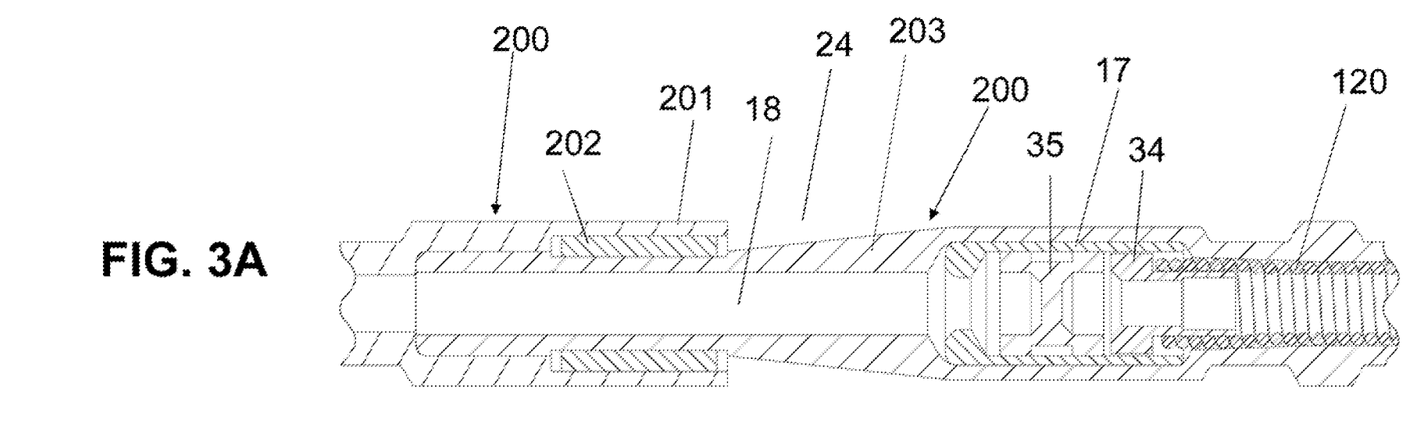
FIGS. 3A and 3B show a sectional illustration of a transition between two segments of the fixing device of the kind in FIGS. 1 and 2 before and after the separation of a segment.
Figure 3B:
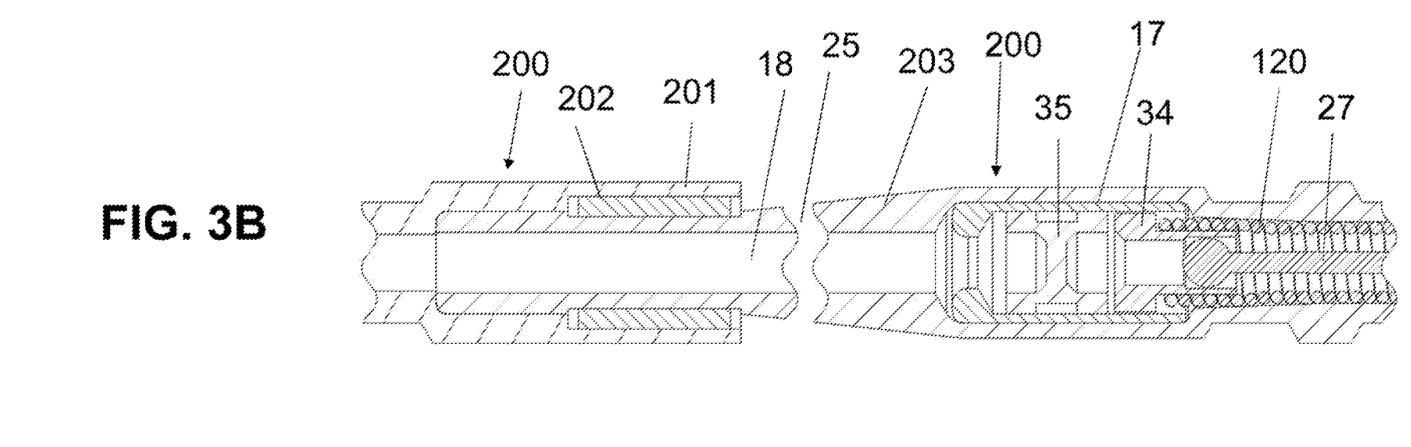
Figure 4:
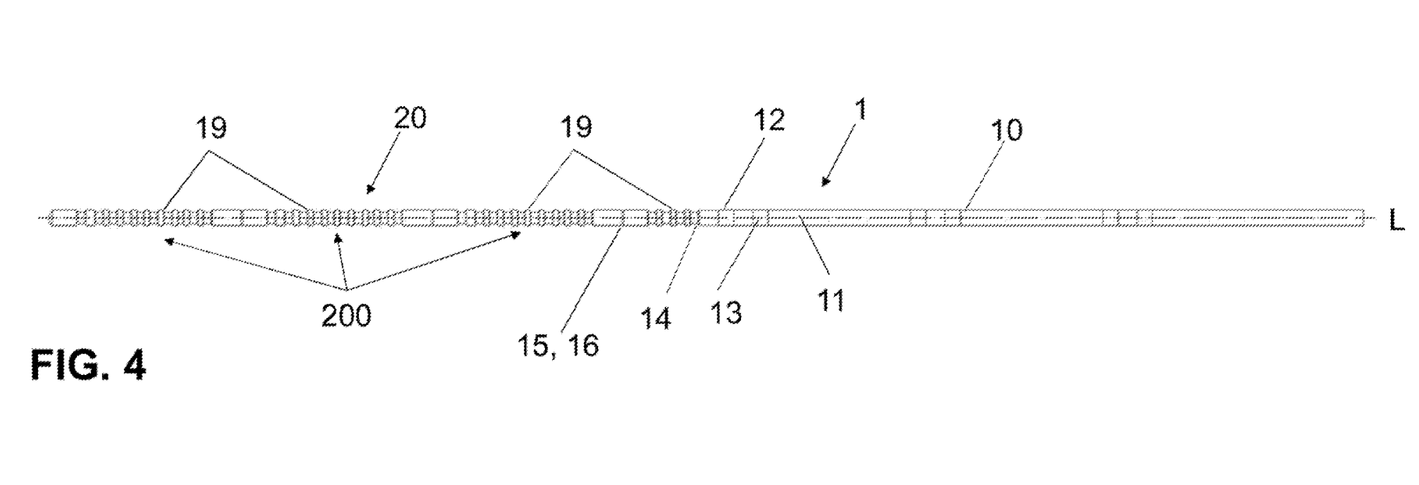
FIG. 4 shows a depiction of a further embodiment of an electrode lead with a fixing device that can be lengthened incrementally.
Figure 5:
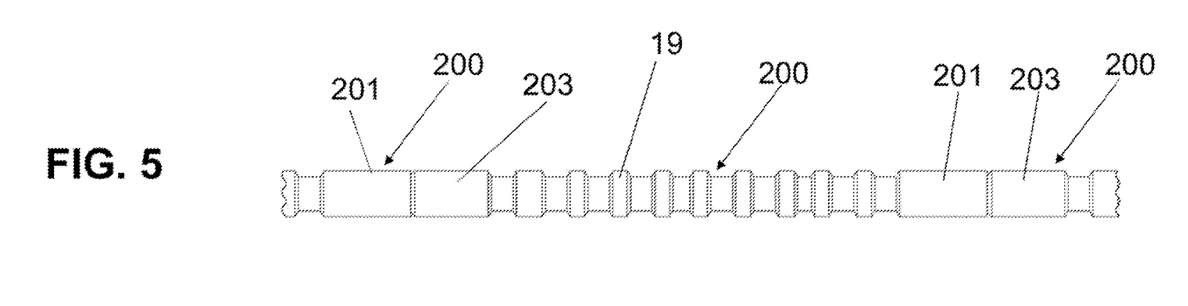
FIG. 5 shows a depiction of a segment of the fixing device according to FIG. 1.

FIG. 1, in conjunction with FIGS. 2, 3A and 3B shows an embodiment of an electrode lead 1 according to the present invention for use in the coronary sinus. The electrode lead 1 has a preferably elongate lead body 10, which extends along a longitudinal axis L and has a distal portion 11 for insertion into the coronary sinus. The electrode lead 1 further has two or also more (for example 3, 4, 5, 6 electrodes or also 2, 3, 4, 5, 6 electrode pairs) electrodes 12, 13 for contacting bodily tissue, which electrodes can be configured in each case as a stimulation electrode or as a sensing electrode. The at least two electrodes 12, 13 are, in particular, annular and are arranged on the distal portion 11 of the lead body 10 distanced from one another in the direction of the longitudinal axis L of the lead body 10. In accordance with the present invention, it is now provided that the electrode lead 1, in order to fix the electrode lead 1 in a blood vessel, has a fixing device 20 extended along the longitudinal axis L and connected to a distal end 14 of the lead body 10, wherein the fixing device 20 has a length along the longitudinal axis L that can be shortened incrementally.

To this end, the fixing device 20 preferably has a plurality of interconnected segments 200 (see FIGS. 1 and 2), wherein each two adjacent segments 200 can be separated from one another in order to shorten the fixing device 20 incrementally. The segments 200 preferably have an identical design here.

As can be seen in FIGS. 2, 3A and 3B, it is furthermore provided that a proximal end portion 201 of a segment 200 is in each case fixedly connected to a distal end portion 203 of an adjacent segment 200. The individual segments 200 of the fixing device 20 are designed here for incremental shortening of the fixing device 20 such that the individual segments 200 can be separated from one another by cutting by means of a cutting tool, for example by means of a scalpel or scissors.

According to FIG. 3, each segment 200, at its proximal end portion 201, has an x-ray marker 202, wherein the position of the x-ray marker 202 along the longitudinal axis L of the fixing device 20 advantageously can be seen by the naked eye. In addition, a different color and/or a different x-ray contrast and/or a different pattern in the x-ray image is advantageously selected for each x-ray marker 202 of a segment 200 of the fixing device 20.

On account of the x-ray markers 202, in the inserted state of the electrode lead 1, the exact position of the fixing device 20 and therefore of the electrodes 12, 13 in the blood vessel, preferably in a vein branch of the coronary sinus, can be determined by means of x-ray imaging. Here, it is advantageous if the electrodes 12, 13 are made of a material or comprise a material that is discernible in the x-ray image. In the case of blood vessels that taper in the distal direction as seen from the electrode lead 1, it may be that the electrodes 12, 13 cannot be advanced far enough due to the length of the fixing device 20. In such a case the number of segments 200 to be removed from the fixing device 20 can be determined by counting the x-ray markers 202.

Following the removal of the electrode lead 1 from the blood vessel, the fixing device 20 of the electrode lead 1 can be shortened outside the body, but during the procedure in the operating theatre, by separating individual segments 200 from the fixing device 20 by means of a cutting tool. The x-ray markers 202 visible to the eye make it possible to locate the separation position 24. In FIGS. 3A and 3B, the x-ray markers 202 are provided, by way of example, at the proximal end portion 201 of the segments 200. In the event that the fixing device 20 is to be shortened by means of a cutting tool, the fixing device 20 is then separated proximally of the visible x-ray marker 202. Due to the now shortened fixing device 20, the electrodes 12, 13 can be advanced further into the blood vessel when the electrode lead 1 is reinserted. At the same time, an optimal position for the electrodes 12, 13 and an optimal fixing position for the electrode lead 1 or the fixing device 20 in the target vein can hereby be selected.

It can be seen in FIG. 3A that the fixing device 20 can be conical in the region of the separation position 24, wherein the narrow end of the cone points in the distal direction and the thicker end of the cone points in the proximal direction in relation to the electrode lead 1. As result of this conical design of the fixing device 20 in the region of the separation position 24, a narrower, distal end 15 of the fixing device 20 formed to a point is formed after the separation 25 (see FIG. 3B) of the segments 200 by a cutting tool. This resultant point of the distal end 15 of the fixing device 20 facilitates the insertion of the distal end 15 of the fixing device 20 of the electrode lead 1 into a catheter and the advancing of the electrode lead 1 into a blood vessel, such as a vein branch of the coronary sinus.

FIGS. 4 to 6B show an alternative embodiment of an electrode lead 1 according to the present invention for use in the coronary sinus. The electrode lead 1 has a preferably elongate lead body 10, which extends along the longitudinal axis L and has a distal portion 11 for insertion into the coronary sinus. The electrode lead 1 furthermore has two or also more (for example 3, 4, 5, 6 electrodes or also 2, 3, 4, 5, 6 electrode pairs) electrodes 12, 13 for contacting bodily tissue, which in each case can be configured as a stimulation electrode or as a sensing electrode. The at least two electrodes 12, 13 are in particular annular and are arranged on the distal portion 11 of the lead body 10 at a distance from one another in the direction of the longitudinal axis L of the lead body 10 accordance with the present invention, it is now provided that the electrode lead 1, in order to fix the electrode lead 1 in a blood vessel, has a fixing device 20 extended along the longitudinal axis L, which fixing device is connected to a distal end 14 of the lead body 10, wherein the fixing device 20 has a length, which can be shortened incrementally, along the longitudinal axis L.

To this end, the fixing device 20, similarly to FIGS. 1 and 2, preferably has a plurality of interconnected segments 200 (see FIGS. 4 and 5), wherein each two adjacent segments 200 can be separated from one another in order to incrementally shorten the fixing device 20. The segments 200 preferably have an identical structure here.

As can be seen in FIGS. 4 to 6B, it is furthermore provided that in each case a proximal end portion 201 of a segment 200 is releasably connected to a distal end portion 203 of an adjacent segment 200. The individual segments 200 of the fixing device 20 are designed here for incremental shortening of the fixing device 20, such that, in order to separate the two adjacent segments 200, a force-fit and/or form-fit connection 16 in the form of a clamped connection or a latched connection 204 or a bayonet connection (not shown in the drawings) is provided between the proximal end portion 201 of a particular segment 200 and a distal end portion 203 of the adjacent segment 200. Furthermore, the connection in question 16, 204 is preferably sealed by means of one or more sealing faces. This seal prevents liquid, such as blood, from infiltrating the lumen 18 of the electrode lead 1.

Figure 6A:
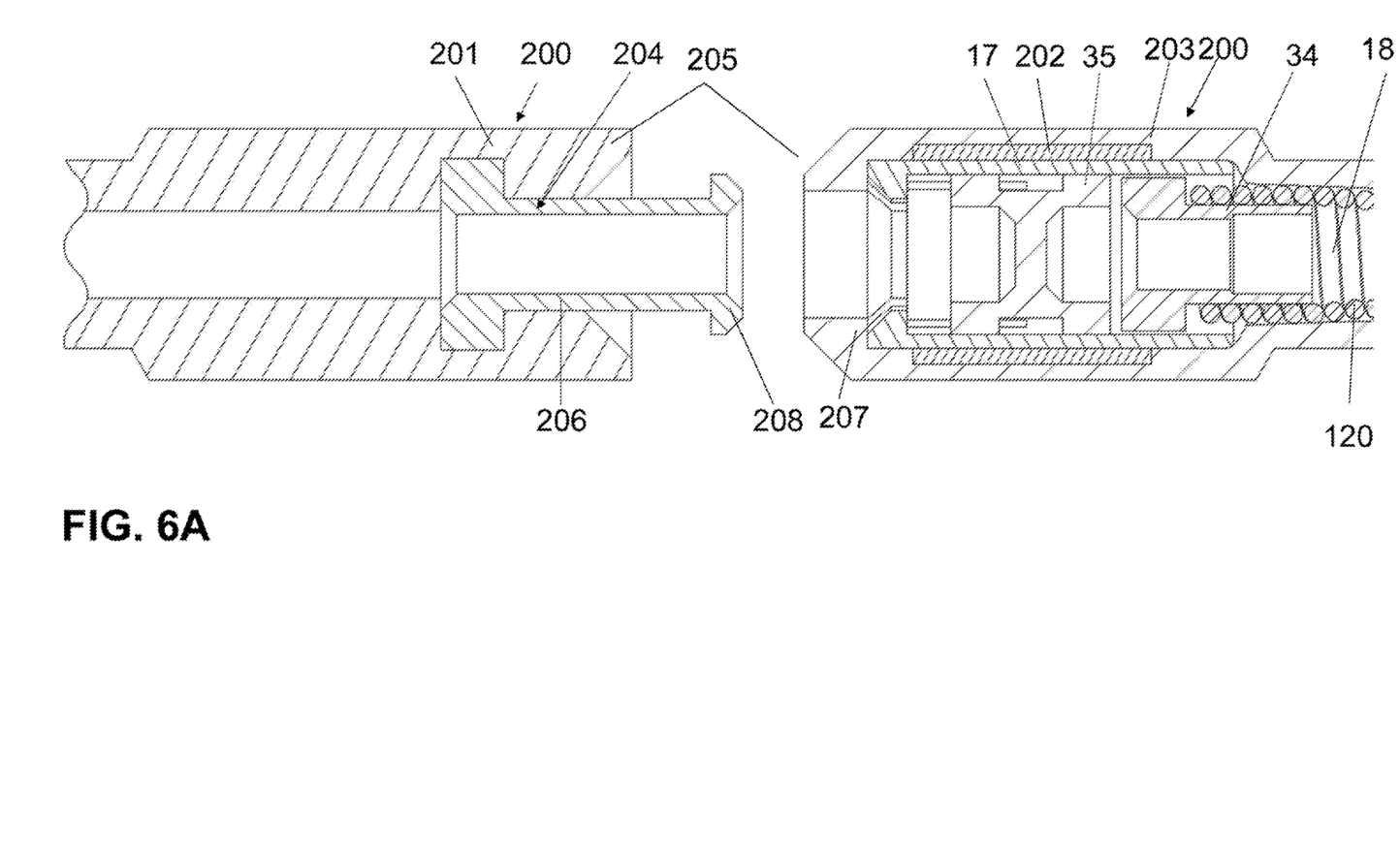
FIGS. 6A and 6B show a sectional illustration of a transition between two segments of the fixing device according to FIGS. 4 and 5.
Figure 6B:
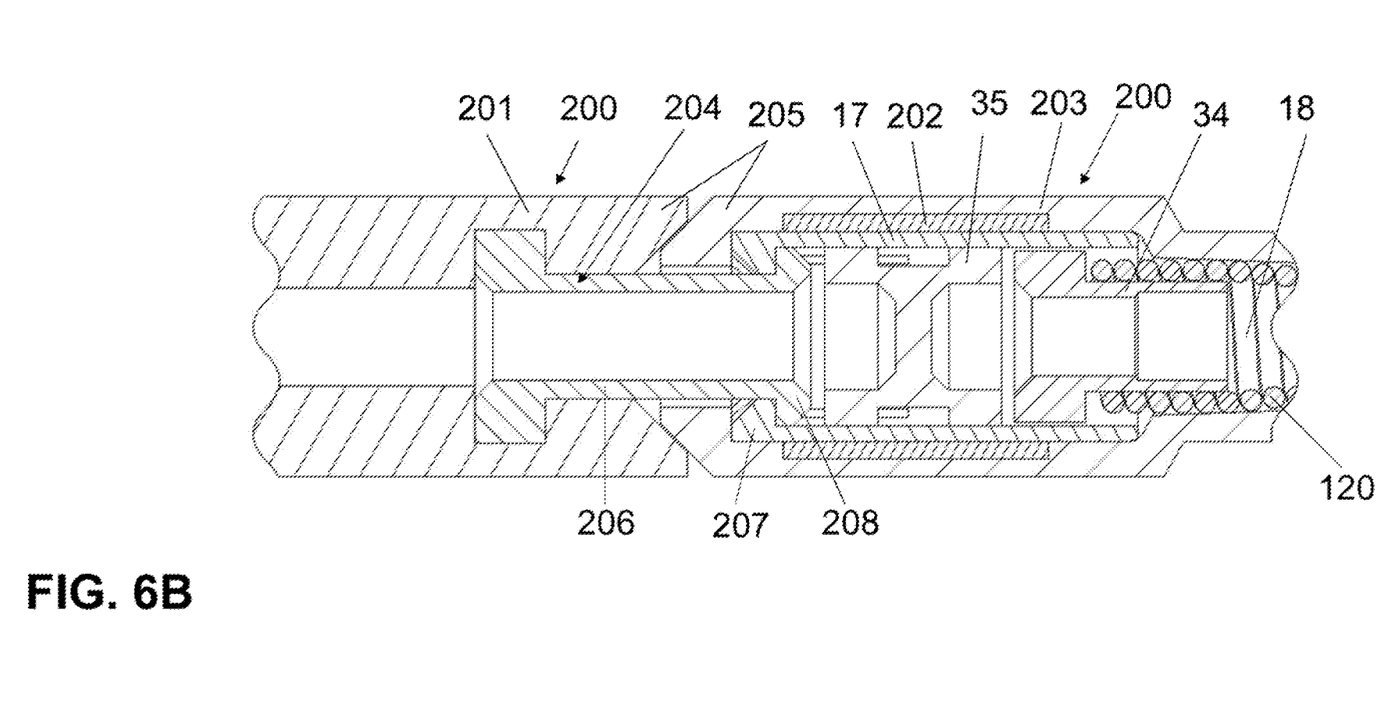

It is furthermore provided that the gap, situated at the connection point, at the surface of the segment 200, has a gap width between the two adjacent segments 200 of at most 0.5 mm, preferably of at most 0.3 mm, and more preferably of at most 0.1 mm.

In order to reduce the width of the gap between each two adjacent segments 200, it is provided that one of the segments 200 has a proximal end portion 201 which with its sealing face 205 adjoins the distal end portion 203 of the adjacent segment 200.

FIGS. 4 to 6B also show an alternative embodiment, in which, in order to incrementally lengthen the fixing device 20, at least one segment 200 or a plurality of segments 200 connectable or connected to one another is provided, wherein the at least one segment 200 or the plurality of segments 200 is connectable to a distal end 15 of the fixing device 20 via a force-fit and/or form-fit connection 16. Here as well, the individual segments 200 may each have an identical structure.

The individual segments 200 can be connected or are connected to one another and to the distal end 15 of the fixing device 20, in particular via a latching connection 204 (or a bayonet connection—not shown in the Figures). Here, the connection in question is preferably sealed by means of one or more seals. This seal prevents liquid, for example blood, from infiltrating the lumen 18 of the electrode lead 1.

In order to produce the latched connection 204 in question, the segment 200 in question, as shown in FIGS. 6A and 6B, can have a latching sleeve 206, which protrudes proximally from the segment 200 and which is designed to be inserted into the distal end portion 203 of the adjacent segment 200 and in so doing to engage behind a latching face 207 of the adjacent segment 200. The latching sleeve 200 for this purpose can have a mushroom-shaped head 208. The latching sleeve 206 or the head 208 are preferably slotted so as to enable them to be latched to one another.

In the above-described embodiment, it is preferably provided (see FIGS. 3A, 3B, 6A, 6B, 8A and 8B) that each segment 200 has a distal end portion 203 which includes a sleeve 17 which is designed to form a stop 34 for a mandrel 27, such that the fixing device 20 can be movable by means of the mandrel 27 and/or can be wedged against the blood vessel by means of the mandrel in order to fix the fixing device 20 in the blood vessel. Since each segment 200 has a sleeve 17 and a stop 34 of this kind, segments 200 can be added or removed in principle arbitrarily, wherein the function of the mandrel is unaffected.

It is furthermore preferably provided that the electrode lead 1, after the separation of all segments 200, in order to fix the electrode lead 1 in a blood vessel, has a fixing device 20 extended along the longitudinal axis L, which fixing device cannot be shortened further in its length and is connected to a distal end 14 of the lead body 10 (see FIGS. 1, 3A, 3B, 4, 8A and 8B). This remaining fixing device 20 preferably includes, likewise at its distal end 15, a sleeve 17, which is designed to form a stop 34 for a mandrel 27, such that the fixing device 20 is movable by means of the mandrel 27 and/or can be wedged against the blood vessel by the mandrel in order to fix the fixing device 20 in the blood vessel.

In order to insert the mandrel 27, the segments 200 of the above-described embodiment of the electrode lead 1, in particular in each case have a lumen 18, wherein the lumens 18, when the segments 200 are connected to one another, form a continuous lumen 18 for receiving the mandrel 27. The mandrel 27 can be inserted here via the lumen 18 of the lead body 10 into the aligned lumens 18 of the segments 200 or the fixing device 20.

Furthermore, a seal 35 arranged in the lumen 18 of the segments 200 is provided in the distal end portion 203 of the segments 200 (see FIGS. 3A, 3B, 6A, 68, 8A and 8B). The seal 35 closes the lumen 18 of the segment 200 so that no bodily fluid, such as blood, can infiltrate the lumen 18 of the segment 200 through the distal opening of the lumen 18 of the segment 200. The seal 35 is ideally arranged in the segment 200 distally of the stop 34. In addition, the seal 35 can be arranged within the sleeve 17 arranged at the distal end portion 203 of the segment 200. The seal 35 can also be arranged at the distal end 15 of the fixing device 20 not further shortenable in its length.

In order to fix the fixing device 20 in the selected blood vessel of the coronary sinus, the segments 200 may furthermore have a surface structure 19 (for example made of silicone) suitable for this purpose (see FIGS. 1, 2, 4, 5, 8A and 8B), which, for example, can be formed by a helical thread or alternately arranged protrusions and indentations.

Furthermore, individual segments 200 or all segments 200 can have a predefined form (not shown in the figures), which enables the segments 200 or the fixing device 20 to be anchored in the selected blood vessel. This predefined form is set straight by a mandrel 27 inserted into the lumens 18, wherein the segment 200 in question assumes the predefined form as soon as the mandrel 27 is removed from the corresponding lumen 18.

The predefined form of the segment 200 can correspond to one of the following forms: a curved form, a helix, an S curve, a meandering structure, a J curve.

A plurality of segments 200 may also have a predefined form which can be set straight as described above, wherein adjacent segments 200 can also together have or form one of the aforementioned predefined forms.

Provided a mandrel 27 is arranged in the continuous lumen 18 of the segments 200, the predefined forms are set straight to give a linear (not curved) form.

A predefined form that one or more of the segments 200 can assume following removal of the mandrel 27 can be furthermore both two-dimensional and three-dimensional.

Figure 7A:
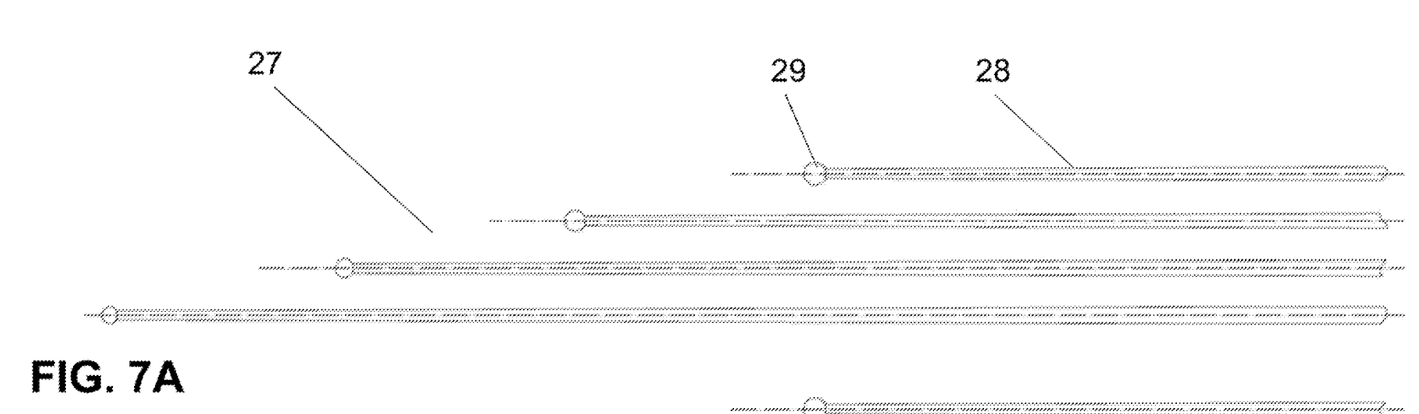
FIGS. 7A and 7B show mandrels with a thrust element.
Figure 7B:
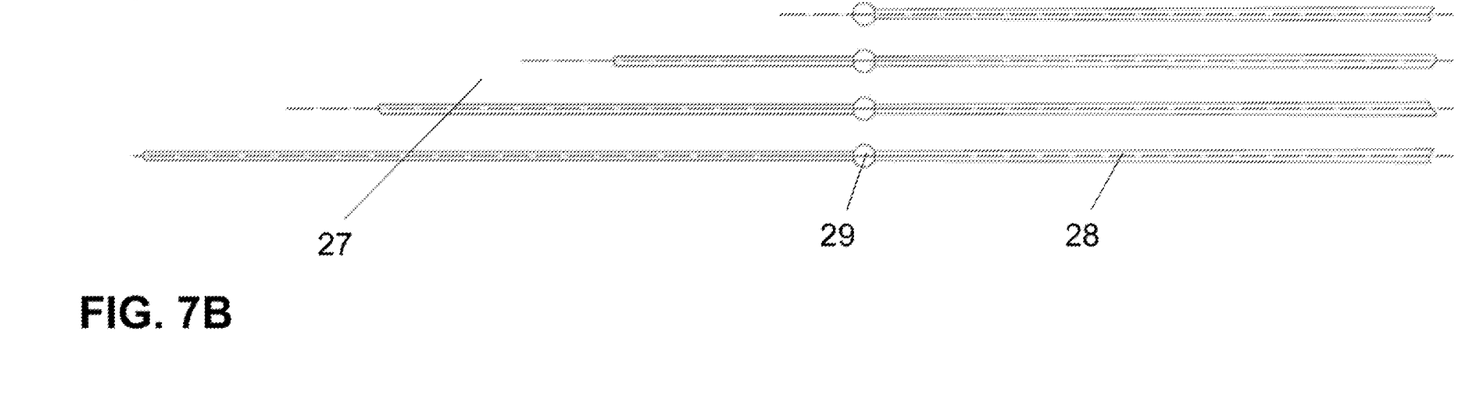

FIGS. 7A and 7B show mandrels 27 that can be used to move the electrode lead 1 into the blood vessel and wedge the electrode lead 1 in the blood vessel. So that the mandrel 27 can engage with a stop 34 arranged in the distal region 11 of the electrode lead 1, the mandrel 27 has a thrust element 29 fastened to its shaft 28 in the vicinity of the distal end or at the distal end of the shaft 28. The thrust element can be embodied in the form of a sphere—as shown by way of example in FIGS. 7A and 7B. The thrust element 29, however, may also have the form of a cylinder or cone arranged coaxially with the shaft 28 of the mandrel 27.

Figure 8A:
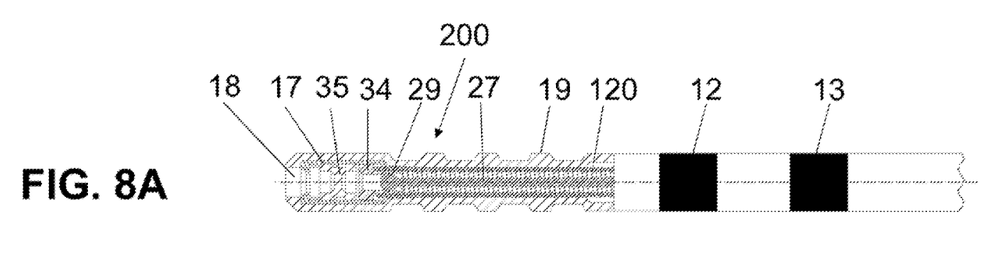
FIGS. 8A and 8B show an electrode lead of FIGS. 1 to 6B with inserted mandrel.
Figure 8B:
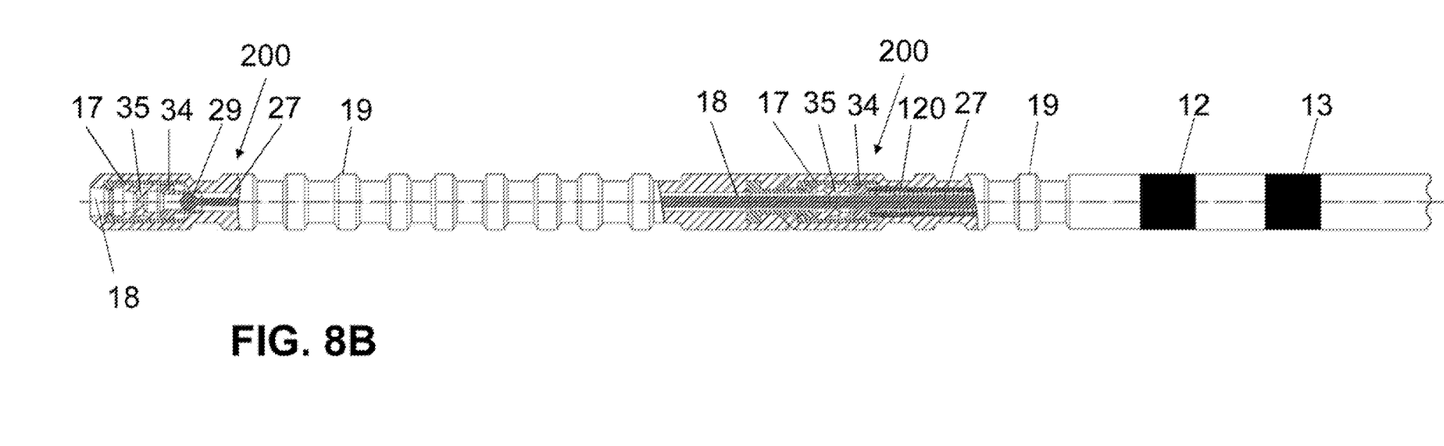

FIG. 8A shows the distal region 11 of an electrode lead 1 with a fixing device 20 that comprises a segment 200. Both the part of the fixing device 20 not further shortenable in its length and the segment 200 have a stop 34, wherein the cross-sectional area of the passages through the stops 34 decreases from a proximal end distally along the length L of the electrode lead 1. The mandrel 27 inserted into the lumen 18 of the electrode lead 1 has a thrust element which can pass through the proximally situated stop 34 and only engages with the distally situated stop 34 of the segment 200. Should the mandrel 27 be intended to be brought into engagement with the stop 34 of the part of the fixing device 20 not further shortenable in its length, as shown in FIG. 8B, a mandrel 27 must be selected that has a thrust element 29 having a larger cross-sectional area than the thrust element 29 of the mandrel 27 shown in FIG. 8A. The mandrel 27 inserted into the lumen 18 of the electrode lead 1 must therefore have a thrust element 29 that cannot pass through the passage of the proximally situated stop 34. If, for example, the passages through the stops 34 for example are embodied as circular axial central bores along the longitudinal direction L of the electrode lead 1, in the case of a manufacturing tolerance of less than 0.1 mm for the diameter of the bore and the diameter of the thrust element 29, the diameter of the passages from stop to stop along the longitudinal axis L of the electrode lead 1 should reduce by at least 0.2 mm.

If the segments 200 that are added to the fixing device 20 in order to lengthen it or that are separated from the fixing device 20 in order to shorten it have stops 34 with passages of differently sized cross-sectional areas, a mandrel 27 must be associated with each segment 200, wherein the thrust element 29 of each segment must be unable to pass through the passage of the stop 34 of this segment 200, but said thrust element 29 must be able to pass through the passages of the stops 34 of the segments 200 arranged proximally of this segment 200. A set of mandrels 27 (see FIG. 7A) is preferably provided for the electrode lead 1, wherein the cross-sectional areas of the thrust elements 29 are tailored accordingly to the passages of the stops 34 of the fixing device 20 and the segments 200 connected thereto.

Alternatively, it is provided that a mandrel 27 used to move the electrode lead 1 in the blood vessel and to wedge it in the blood vessel has a thrust element 29 along its shaft 28, such that the mandrel 27 engages with the stop 34 arranged at the proximal end 15 of the fixing device 20 of the electrode lead 1 when the mandrel 27 is introduced into the lumen 18 of the electrode lead coming from the proximal direction, such that the electrode lead 1 can be advanced by the mandrel 27 along its longitudinal axis L in the distal direction. The mandrel 27 is preferably designed here such that the part of the shaft 28 of the mandrel arranged distally of the thrust element 29 corresponds in its length to the length of the segments 200 connected to the electrode lead 1. If the electrode lead 1 is shortened by separation of a segment 200 from the fixing device 20 or is lengthened by addition of a segment 200 to the fixing device 20, the part of the shaft 28 of the mandrel 27 arranged distally of the thrust element 29 thus preferably must be adapted in its length to the modified length of the fixing device 20. If the mandrel 27 is correctly selected, the part of the shaft 28 of the mandrel 27 arranged distally of the thrust element 29 therefore does not protrude beyond the distal end 15 of the fixing device 20—even during the insertion of the electrode lead 1. A set of mandrels 27 (see FIG. 7B) in which the lengths of the parts of the shaft 28 of the mandrel 27 are tailored accordingly to the length of the fixing device 20 and the segments 200 connected thereto is preferably provided for the electrode lead 1.

FIGS. 3A, 3B, 6A, 6B, 8A and 8B show that the electrodes 12, 13 are connected to an electrical conductor 120, which is arranged in an interior of the lead body 10, wherein the electrical conductor 120 extends helically around the lumen 18 of the lead body 10, which is designed to receive a mandrel 27. If the at least two electrodes 12, 13 are connected to the connection device 3 separately by independent electrical conductors 120, the two electrical conductors 120—as shown—can thus extend in a manner arranged co-radially relative to one another. Here, the individual electrical conductors 120 are in particular wound, insulated from one another, to form a multiple helix, in which the two electrical conductors 120 form congruent helices of equal diameter and equal pitch, which engage in one another. Alternatively, the conductors 120 can also be arranged coaxially with one another and can extend around the lumen 18 of the lead body 10, which is designed to receive a mandrel 27. Furthermore, the electrical conductors 120 can also be formed as conductive cords.

In order to produce a releasable connection to a pulse generator, such as a heart stimulator for CRT therapy, the lead body 10, at its proximal end 2, has a connection device 3 (see FIG. 1), which can be configured in the form of a plug 3 (for example in the form of an IS-1 or IS4 plug). Here, the corresponding electrical conductor is connected to an associated contact (not shown) of the connection device 3.

The present invention also relates to a medical kit with an electrode lead 1 according to the present invention, wherein the kit also has a set of matching mandrels. In the case of electrode leads 1 that can be lengthened, the kit additionally has corresponding segments 200 for lengthening the fixing device 20 of the electrode lead 1. Depending on the number of segments 200 of the fixing device 20, this (or the electrode lead 1) has a certain (discrete) length along the longitudinal axis L. The kit now has preferably precisely one mandrel for each adjustable length, which mandrel then has the appropriate length for moving and wedging the fixing device 20 or the electrode lead 1.

With current CRT electrodes, CRT therapy is not always possible optimally for all anatomical conditions. The solution according to the present invention, by way of a variable, incrementally adjustable length of the fixing device, offers an optimal implantation site and, at the same time, a reliable fixing of the electrode lead 1 in all anatomical vein constellations. This allows in particular the use of economical 1- or 2-pole electrodes 12, 13. Furthermore, the surgeon can adjust the fixing length as required, intraoperatively as necessary.

It will be apparent to those skilled in the art that numerous modifications and variations of the described examples and embodiments are possible in light of the above teachings of the disclosure. The disclosed examples and embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. An electrode lead for the coronary sinus, comprising:
   a lead body having a longitudinal axis and a distal portion for insertion into the coronary sinus, and
   at least one electrode for contacting bodily tissue, wherein the at least one electrode is arranged on the distal portion of the lead body,
   wherein the electrode lead, in order to fix the electrode lead in a blood vessel, has a fixing device, which is connected to a distal end of the lead body and includes an axial length extending along the longitudinal axis of the lead body, wherein the fixing device is designed to be shortened incrementally or lengthened incrementally along its axial length, and
   wherein the fixing device, in order to shorten the fixing device incrementally, has a plurality of interconnected segments releasably interconnected axially to one another and extending along the axial length of the lead body, wherein each two adjacent segments can be separated from one another in order to incrementally shorten the fixing device along its axial length.

2. The electrode lead according to claim 1, wherein of each two adjacent segments, one of the segments has a proximal end portion, which is releasably connected via a sealing face to a distal end portion of the adjacent other segment.

3. The electrode lead according to claim 1, wherein of each two adjacent segments, one of the segments has a proximal end portion, which, in order to separate the two adjacent segments, is releasably connected to a distal end portion of the adjacent other segment via a clamped connection.

4. The electrode lead according to claim 3, wherein of each two adjacent segments, one of the segments has a proximal end portion, which is connectable or connected to a distal end portion of the adjacent other segment via a force-fit and/or form-fit connection.

5. The electrode lead according to claim 1, wherein each segment has a distal end portion, which has a sleeve, which is designed to form a stop for a mandrel, such that the fixing device is movable by means of the mandrel and/or can be wedged against the blood vessel in order to fix the fixing device in the blood vessel.

6. The electrode lead according to claim 1, wherein the segments have a surface structure in order to be anchored in the blood vessel.

7. A medical kit with an electrode lead according to claim 1 and with a plurality of mandrels of different length for insertion into the electrode lead.

8. The electrode lead according to claim 1, wherein the segments each have a lumen, wherein the lumens in an interconnected state of the segments form a continuous lumen for receiving a mandrel.

9. The electrode lead according to claim 8, wherein at least one of the segments of the fixing device has a predefined form for fixing the fixing device in the blood vessel, which form can be set straight by inserting a mandrel into the lumen of the at least one segment, wherein the at least one segment is designed to assume the predefined form following removal of a mandrel from the lumen of the at least one segment.

10. An electrode lead for the coronary sinus, comprising:
a lead body having a longitudinal axis and a distal portion for insertion into the coronary sinus, and
at least one electrode for contacting bodily tissue, wherein the at least one electrode is arranged on the distal portion of the lead body,
wherein the electrode lead, in order to fix the electrode lead in a blood vessel, has a fixing device, which is connected to a distal end of the lead body and includes an axial length extending along the longitudinal axis of the lead body, wherein the fixing device includes a plurality of interconnected segments releasably interconnected axially to one another and extending along the axial length of the lead body, wherein the fixing device is designed to be shortened incrementally or lengthened incrementally along its axial length, and
wherein in order to incrementally lengthen the fixing device in its axial direction, at least one additional segment or a plurality of additional interconnectable or interconnected segments is provided, wherein the at least one additional segment or the plurality of additional segments is releasably connectable to one of the plurality of interconnected segments positioned at a distal end portion of the fixing device via a force-fit and/or form-fit connection.

\* \* \* \* \*